United States Patent [19]

Atwood et al.

[11] 3,981,041

[45] Sept. 21, 1976

[54] SPONGE IRRIGATION SYSTEM FOR AUTOMATIC ANALYSIS APPARATUS

[75] Inventors: John G. Atwood, Redding; Lucian C. Ducret, Riverside, both of Conn.

[73] Assignee: The Perkin-Elmer Corporation, Norwalk, Conn.

[22] Filed: Aug. 22, 1974

[21] Appl. No.: 499,856

[52] U.S. Cl. .............................................. 15/302
[51] Int. Cl.² ........................................ A47L 7/00
[58] Field of Search ............... 15/301, 302; 23/253, 23/259

[56] References Cited
UNITED STATES PATENTS 3,628,213 12/1971 Ramo ............................. 15/301 X
3,753,657 8/1973 Downing et al. ................. 23/253 R

*Primary Examiner*—Leonard D. Christian
*Assistant Examiner*—C. K. Moore
*Attorney, Agent, or Firm*—S. A. Giarratana; F. L. Masselle; J. M. O'Meara

[57] ABSTRACT

A sponge irrigation system for automatic analysis apparatus in which wiping sponges are used to wipe off the tips of pipettes, probes and so on to accurately control drops on the tips thereof, in which irrigation fluid for maintaining a clean irrigated sponge is sequentially provided to each of the sponges in the system with vacuum means used to sequentially draw from the sponges contaminated liquid, thereby assuring that each sponge is properly and equally irrigated.

4 Claims, 4 Drawing Figures

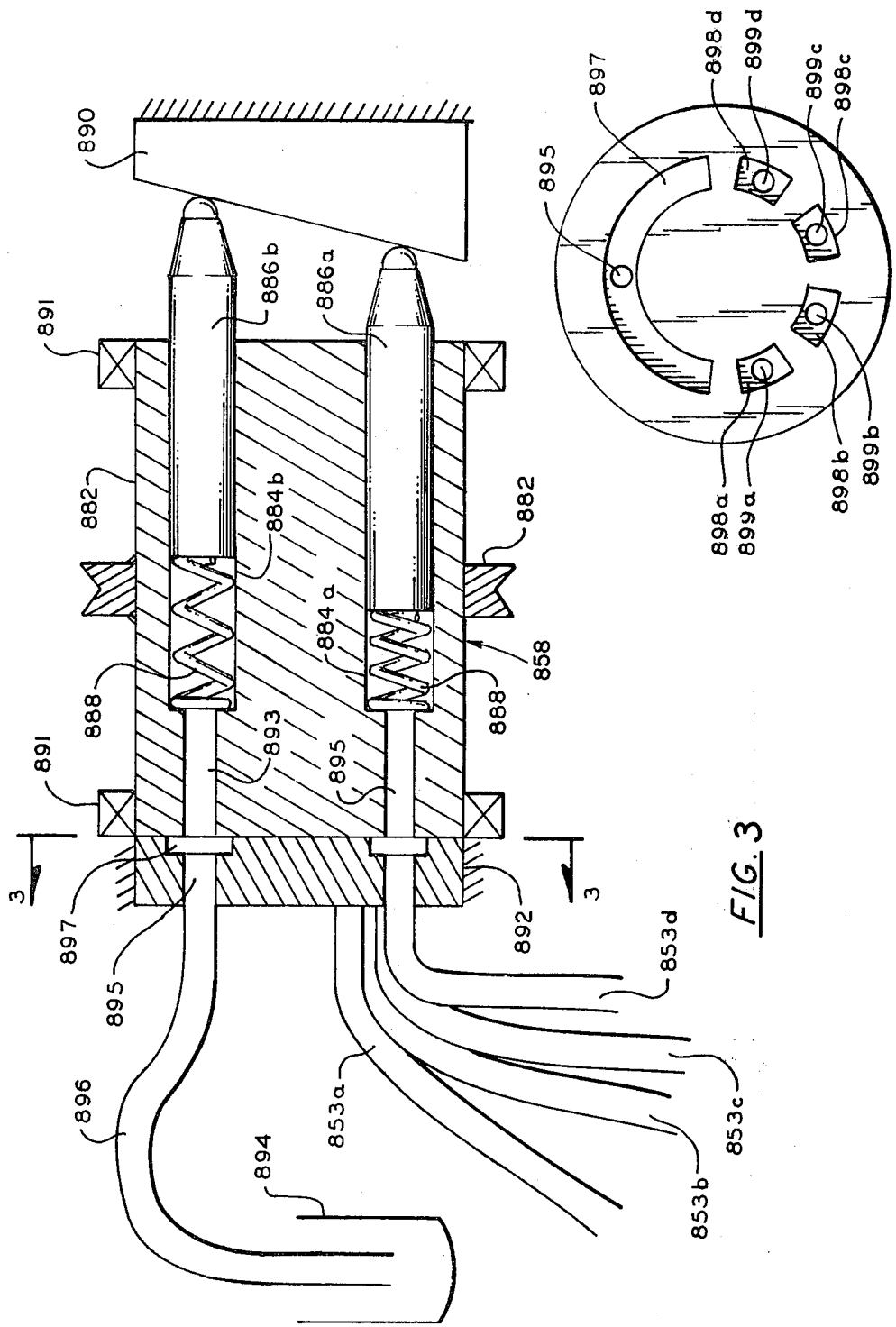

SPONGE IRRIGATION SYSTEM FOR AUTOMATIC ANALYSIS APPARATUS

BACKGROUND OF THE INVENTION

This invention relates to automatic analysis apparatus in general and more particularly to an improved sponge irrigation system for use in such analysis apparatus.

In a copending application of John G. Atwood et al, Ser. No. 594,951 filed July 10, 1975 as a continuation of now abandoned application Ser. No. 499,602, filed Aug. 22, 1974 and assigned to the same assignee as the present invention, a completely automatic kinetic analysis apparatus is disclosed. In that apparatus sponge wipers are employed to wipe off the tips of pipettes, probes, etc., to control the size of the drop on the tip thereof and to reduce sample carry over. For such a spong wiping system to be effective the sponges must be irrigated so that contamination is removed and a fresh supply of irrigating liquid provided to each sponge. In the prior art such has been accomplished in similar devices by periodically removing and washing the sponge. Clearly in a completely automated apparatus which is designed for unattended use over extensive periods of time such a solution is unacceptable.

In view of this the need arises to irrigate the sponges continually supplying fresh irrigation liquid thereto and removing contaminated liquid. On the surface this might suggest simply supplying each of the sponges with a liquid supply and drawing liquid away therefrom with common means. Such is not effective because of different physical locations of the sponges at different distances from a source and unequal irrigation occurs with only the sponge nearest the source being properly irrigated. Of course another solution would be to separately irrigate each sponge. However, such becomes unduly expensive.

Thus, the need for a simple and effective device which can equally irrigate a plurality of sponges becomes evident.

SUMMARY OF THE INVENTION

The present invention provides such an irrigation device which permits adequately and equally irrigating a plurality of sponges.

The sponges used in the present invention are each contained in a plastic enclosure having suitable openings for a probe or pipette to pass therethrough. The enclosure, which is made of plastic has an inlet connection and outlet connection to which appropriate tubing can be attached. The irrigation system of the present invention includes means to sequentially provide a clean supply of irrigation fluid to each of the sponges and also means to sequentially draw from the sponges contaminated irrigation fluid and to direct that contaminated fluid to waste. The supply means comprise a water pump and distributor which distributes the water from the pump to each of the sponges in sequence. Similarly, a vacuum distributor sequentially couples each of the sponges to a vacuum pump to draw therefrom contaminated fluid. Through these measures each of the sponges is equally irrigated in a simple fashion.

BRIEF DESCRIPTION OF THE DRAWINGS

FIG. 3 is a sectional view illustrating the water pump of FIG. 1.

FIG. 4 is a section on line 3—3 of FIG. 3.

DETAILED DESCRIPTION OF THE PREFERRED EMBODIMENT

Figure 1:
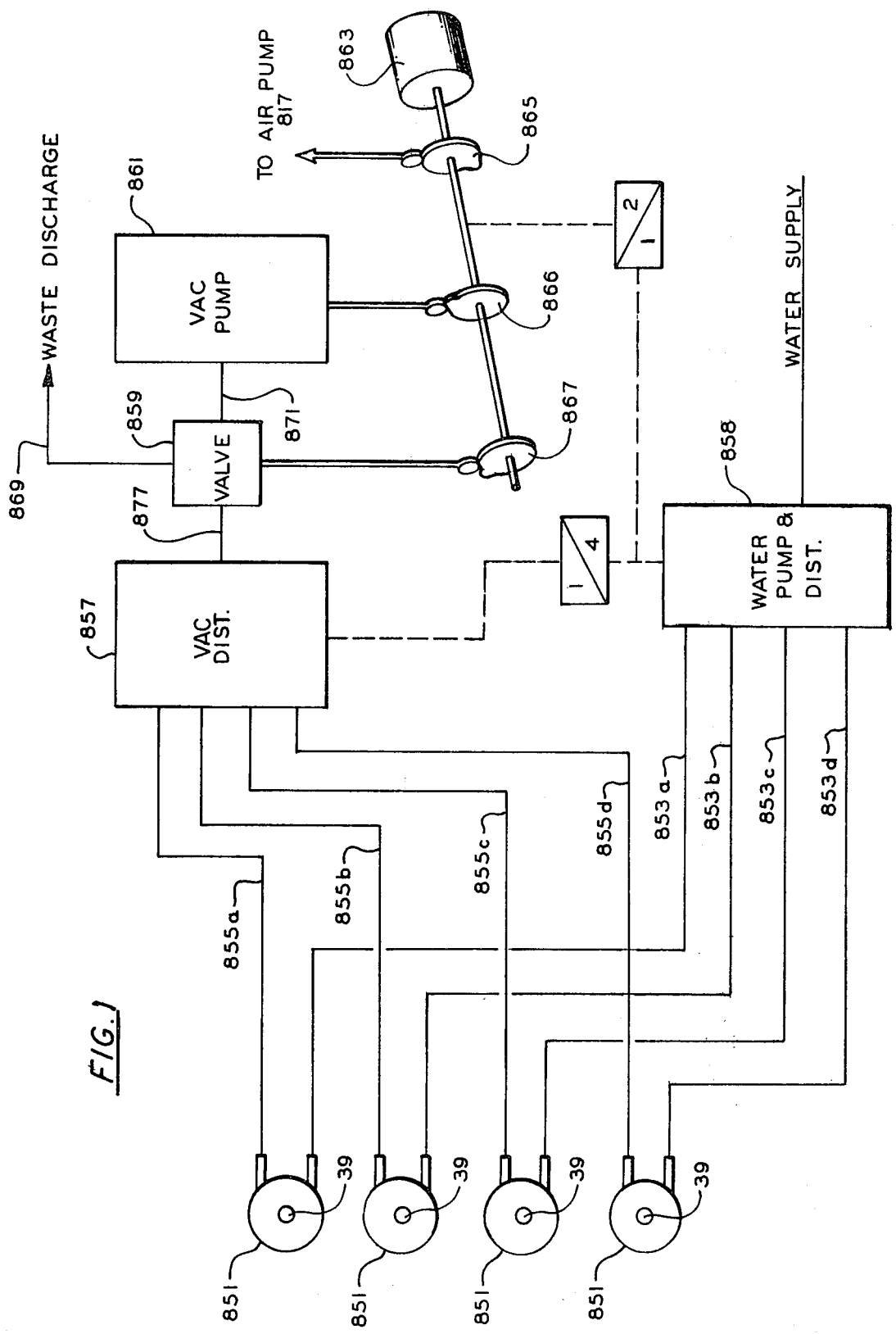
FIG. 1 is a block diagram illustrating the sponge irrigation system of the present invention.

In the automatic system of the above referenced copending application, pipettes or probes are passed through sponges 39 in plastic containers (851) for the purpose of wiping off any drops of liquid thereon to maintain accuracy in the system. To insure proper operation of this portion of the system the water or other irrigation fluid used in the sponges must be constantly circulated, i.e., the water which has become contaminated with reagent, sample or the like must be removed and clean water provided. In principle, this is done by supplying water under pressure to the sponges and removing water therefrom with a vacuum. However, it will be recognized that an ideal system will not be obtained if the various sponges are all just connected together to a pressure source and vacuum source. If such is attempted the sponge closest or the one having the least resistance will get all the circulation whereas no circulation will occur through the others. Thus, it is necessary that the sponges be individually irrigated in sequence in order to insure that each has adequate change of liquid. A block diagram of the system of the present invention for accomplishing this is shown on FIG. 1. Each of the sponge holders 851 is a plastic case having two ports formed therein. Enclosed within the plastic case is a sponge 39. One line from each of the sponge holders 851, i.e., the lines designated 853a through d is provided to a water pump and distributor arrangement. The other lines designated 855a through d are provided to a vacuum distributor 857, the outlet of which is coupled through a valve 859 to a vacuum pump 861. A motor 863 has on its shaft cams 865, 866 and 867. The cam 865 drives an air pump 817 used for other purposes. The cam 866 drives the vacuum pump and the cam drives the valve 859. The motor shaft is coupled through a two-to-one reduction to the water pump and distributor 858 and through an additional four-to-one reduction to the distributor 857. In the preferred embodiment, this is done using belts and pulleys. The water pump and distributor to be described in more detail below sequentially pumps out water drawn in through a water supply line to the lines 853a, b, c and d to supply equal amounts of water to the sponge holders 851. Similarly, the vacuum pump sequentially, through rotation of the distributor 857, draws on each of the lines 855a through d to draw out contaminated water. During the cycle in which the vacuum pump is drawing in, valve 859 couples the vacuum pump to the distributor 857. Water is drawn into the line 871 between the valve and the vacuum pump. As the vacuum pump expels, the valve couples the vacuum pump to the line 869 connected to a waste discharge, thereby forcing out the water drawn in during the vacuum cycle.

Figure 2:
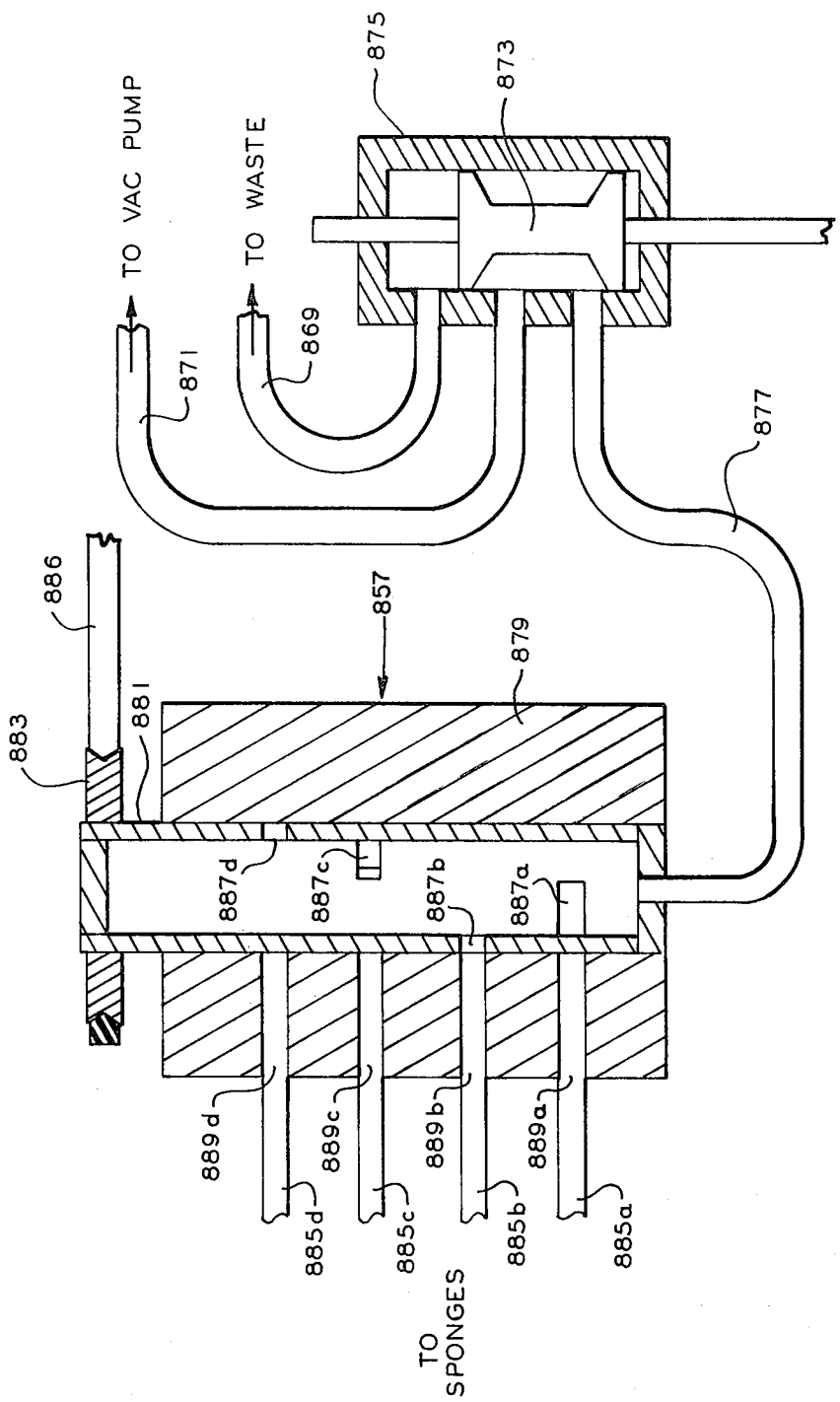
FIG. 2 is a sectional view illustrating the vacuum distributor of FIG. 1.

FIG. 2 illustrates the distributor and the valve arrangement. In the position shown, the line 871 between the valve and the vacuum pump is coupled by the valve spindle 873 to the outlet line 877 which is connected to the distributor 857. The distributor comprises an outer casing 879 with a cylindrical opening therein in which an inner cylinder member 881 can rotate. On top of member 881 is a pulley 883 driven by a belt 886 connected to the motor 863 or connected to the water pump and distributor 858 of FIG. 1. The cylinder 881 contains a plurality of four openings designated 887a, b, c, and d. When properly positioned, they mate with corresponding ports 889a through d to sequentially connect the vacuum input on line 877 to each of the lines 855a through d so that each of the sponges is drawn on equally. After a cycle of drawing in by the vacuum pump, the valve spindle 873 is moved upwardly to couple the lines 869 and 871. Now, as the vacuum pump expels, water drawn into the line 871 during the vacuum cycle is discharged through the lines 869 to waste.

The water pump and distributor 858 of FIG. 1 is shown on FIG. 3. The pump comprises a cylindrical block 880 in which two cylinder bores 884a and 884b are formed. Generally cylindrical piston members 886a and 886b are slidably fitted in bores 884a and 884b, respectively. Springs 888 in cylinders 884a and 884b urge pistons 886a and 886b out of the cylinders so that the outer ends of the pistons, carrying bearing balls for the purposes, abut an inclined surface of a fixed "wobble" (or "swash") plate 890, the surface being a skew plane with respect to the axis of cylindrical block 880. Cylinder block 880 is supported for rotation about its longitudinal axis in conventional bearing means 891. Ports 893 and 895 in block 880 extend from the head end of cylinder bores 884a and 884b, respectively, to the proximal end face of the block on which is fixed a distributor plate 892. A plan view of the inside of distributor plate 892 is shown in FIG. 4. It includes an inlet port 895 which opens into an arcuate channel 897 extending approximately 180° of the plate. Disposed on an arc concentric, and of equal radius, to channel 897 are four additional channels 898a through d, equiangularly spaced and jointly defining an arc of approximately 180°. Opening into each arcuate channel 898a through 898d is a respective port 899a through 899d. Reverting to FIG. 3, port 895 is coupled to a line 896 leading to a water container 894. The ports 899a through d are coupled respectively to the lines 853a through 853d shown on FIG. 1. As the block 881 rotates, one of the pistons 885a, b, etc. (say, 885b), during the portion of the cycle when the port 893 is in communication with the channel 897, retracts drawing water into the cylinder from the container 894. During the remainder of its cycle, it will then sequentially pump water out of each of the ports 899a through d by pumping water to their associated channels 898a through d as it travels over that sector of the distributor plate. While the piston 885b is drawing water in, the piston 885a will be pumping water out in the same manner.

Thus, an improved irrigation system for sponges used in analysis apparatus has been shown. Although specific embodiments have been illustrated and described, it will be obvious to those skilled in the art that various modifications may be made without departing from the spirit of the invention which is intended to be limited solely by the appended claims.

What is claimed is:
1. Sponge irrigation apparatus for irrigating a plurality of wiping sponges used in analysis apparatus comprising:
   a. means at least partially enclosing each sponge to be irrigated said means having an inlet and an outlet;
   b. means to sequentially supply an irrigation fluid to each of said enclosing means;
   c. means to sequentially draw contaminated irrigation fluid from said enclosing means.
2. Apparatus as in claim 1 wherein said means to sequentially supply irrigation fluid to each of said means comprises a pump and distributor having a number of outlets equal to the number of sponges with each outlet coupled to a respective inlet of a sponge holding means, said pump and distributor being arranged to sequentially supply water to each of said inlets.
3. Apparatus as in claim 2 wherein said means for drawing contaminated irrigation fluid from said sponges comprises:
   a. a vacuum pump;
   b. a vacuum distributor;
   c. a valve selectively coupling the inlet of said vacuum pump to said distributor and a waste discharge;
   d. said distributor having a number of inlets equal to the number of sponges with the respective inlets coupled to respective outlets of said holding means; and
   e. means driving said vacuum pump and valve such that said valve couples said vacuum pump to said waste discharge on its discharge stroke and to said vacuum distributor on its intake stroke.
4. Apparatus as in claim 3 wherein said irrigation fluid is water.

* * * * *